United States Patent [19]

Claus et al.

[11] 4,039,636

[45] Aug. 2, 1977

[54] MAGNESIUM DIALKYL PHOSPHATES AND THEIR PREPARATION

[75] Inventors: Kenneth G. Claus, Lake Jackson, Tex.; Jack A. Rogers, Midland, Mich.

[73] Assignee: The Dow Chemical Company, Midland, Mich.

[21] Appl. No.: 374,458

[22] Filed: June 28, 1973

[51] Int. Cl.² .............................................. C07F 9/11
[52] U.S. Cl. .................................. 260/963; 260/987
[58] Field of Search ............................. 260/963, 987

[56] References Cited

U.S. PATENT DOCUMENTS

| | | | |
|---|---|---|---|
| 2,228,659 | 1/1941 | Farrington et al. | 260/963 X |
| 3,033,889 | 5/1962 | Chiddix et al. | 260/987 X |
| 3,117,152 | 1/1964 | Michaels | 260/987 X |

*Primary Examiner*—Richard L. Raymond
*Attorney, Agent, or Firm*—Glwynn R. Baker

[57] ABSTRACT

Magnesium dialkyl phosphates capable of thickening or gelling nonpolar organic solvents are prepared by reacting a dialkyl acid phosphate with a magnesium oxide, hydroxide, or carbonate in organic solvent solution in the presence of a small amount of water within defined limits of time, temperature, mole ratios of reactants, and size of alkyl groups. The products are useful as thickening agents and vapor pressure depressants for nonpolar solvents.

4 Claims, No Drawings

MAGNESIUM DIALKYL PHOSPHATES AND THEIR PREPARATION

BACKGROUND OF THE INVENTION

The present invention concerns a class of magnesium organic phosphates having unusual physical properties and a process for making these substances.

Magnesium dialkyl phosphates have been prepared in the past as white solids by reacting the corresponding sodium salt in an aqueous medium with a magnesium compound such as magnesium hydroxide or magnesium chloride, see Japanese Pat. No. 16670 (1965) and U.S. Pat. No. 2,228,659. These water insoluble salts have been used as additives to improve the dyeability of polyacrylonitrile and as lubricating oil additives to increase resistance to thermal degradation and to reduce wear and corrosion.

SUMMARY OF THE INVENTION

It has now been found that products having considerably different physical properties from known magnesium dialkyl phosphates are obtained when a basic magnesium compound such as the oxide, hydroxide, or carbonate is reacted under particular conditions with a dialkyl acid phosphate of the formula

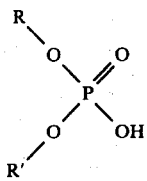

wherein R is an alkyl radical of about 1–6 carbon atoms, R' is an alkyl radical of about 10–20 carbon atoms, and R and R' together contain about 12–24 carbon atoms. The reaction conditions necessary to obtain the different results include using a molar excess of phosphate over the magnesium, limiting the reaction time to about 1–90 minutes, at a temperature of about 100°–190° C., and reacting in the presence of about 2–6 moles of water per mole of magnesium, including the water of reaction, the reaction being carried out in an inert nonpolar organic solvent. Under these conditions, the magnesium salt product is apparently a kind of polymeric species rather than the simple salt previously known and it dissolves in the organic reaction medium to thicken it and form an elastic gel.

DETAILED DESCRIPTION

Dialkyl hydrogen phosphates within the scope of the invention include decyl ethyl hydrogen phosphate, tetradecyl methyl hydrogen phosphate, tert-butyl cetyl hydrogen phosphate, isopropyl stearyl hydrogen phosphate, hexyl tetradecyl hydrogen phosphate, eicosyl propyl hydrogen phosphate, dodecyl pentyl hydrogen phosphate, and others within the definition of the above formula. Surprisingly, apparently very similar compounds such as dioctyl hydrogen phosphate and didodecyl hydrogen phosphate do not react under the conditions of the invention to give a magnesium salt capable of gelling solvents.

Solvents useful in the process and which are gelled by the magnesium organic phosphate product are normally liquid, aliphatic, cycloaliphatic, and aromatic hydrocarbons and their liquid chlorinated derivatives. Representative solvents are pentane, octane, mixtures such as gasoline and kerosene, cyclohexane, cyclopentane, benzene, toluene, xylene, carbon tetrachloride, ethylene dichloride, trichloroethylene, hexyl chloride, chlorobenzene, o-chlorotoluene, and the like. Because of their capacity to thicken or gel such solvents, the magnesium salt products of the invention are particularly useful to decrease the flammability of fuels such as gasoline and kerosene and to minimize odors or toxic vapors during handling of other solvents listed above.

Temperature and time of reaction are critical features of the process. A reaction temperature of about 120°–150° C. and a reaction time of about 5–40 minutes are preferred. Temperatures below about 100° C. give the nongelling form of the magnesium salt whereas temperatures above the 190° C. upper limit previously specified are not practical. Reaction times longer than about 1.5 hours apparently result in the breakdown of the gelling form of the magnesium salt so that only the previously known form is obtained.

It is also necessary for successful operation of the process to react at least a slight molar excess of dialkyl hydrogen phosphate with the magnesium compound. Preferably, about 1.5–3 moles of phosphate are reacted per mole of magnesium. A specific maximum ratio of phosphate cannot be defined but a practical limit is about 4 moles per mole of Mg.

A final critical and necessary feature of the process is the presence of a small proportion of water in the reaction mixture. The minimum quantity necessary is about 2 moles per mole of magnesium and this can be supplied by the water of reaction when the magnesium compound reacted is $Mg(OH)_2$. However, water must be added when MgO or $MgCO_3$ is reacted and, preferably, more water is added in any case to a maximum of about 6 moles of total water per mole of magnesium.

EXAMPLE 1

Dodecyl isopropyl hydrogen phosphate was prepared by slowly adding a mixture of 0.2 g. mole each of 1-dodecanol and isopropyl alcohol to a stirred slurry of 0.1 g. mole of $P_2O_5$ in 100 ml. hexane, holding the temperature of the reaction mixture below its boiling point by use of a water bath. After the addition was complete, stirring was continued until the mixture was clear and then the hexane was distilled off, the last portion under reduced pressure. The product was a clear, colorless liquid which crystallized slowly into a waxy, white solid. It was primarily the desired mixed ester with small amounts of the two symmetrical diesters.

A solution of 5.0 g. of the ester product in 100 g. of kerosene was stirred and heated to 120° C. in a flask equipped with a reflux condenser. At this point, 0.4 g. of magnesium hydroxide was added rapidly. Droplets of water soon began to form on the inside walls of the flask and condenser. After 5 minutes of reaction at 120° C., an additional five drops of water was added to the reaction mixture and stirring was continued at that temperature for another 15 minutes, whereupon the mixture became a clear gel. The gel was cooled slowly to room temperature, becoming a viscous, elastic liquid in the process. The liquid was "stringy," i.e., stringy tails formed when drops fell from a medicine dropper.

Other magnesium dialkyl phosphates were prepared generally as described in the above example by reacting the dialkyl hydrogen phosphate with magnesium oxide or magnesium hydroxide. When the oxide was the magnesium source, slightly more water was added to the reaction mixture but the total water added in all cases was less than 1 gram for the quantities of reactants shown. Hydrocarbon solvents such as toluene, xylene, kerosene and the like are suitable reaction media, also inert chlorinated hydrocarbons such as 1,1,2-trichloroethane, perchloroethylene and chlorobenzene. Other such solvents with lower boiling points can be used but require reaction under pressure to maintain the reaction temperature above 100° C.

The dialkyl hydrogen phosphate starting materials were also prepared generally as described above by reacting $P_2O_5$ with the mixed alcohols when the two alcohols had significantly different reactivities or with the alcohols separately when their reactivities were similar. In a few cases when thermal decomposition of the acid phosphate ester was a problem, methylene chloride was used in place of hexane as the reaction medium.

The magnesium dialkyl phosphates of this invention can be isolated as solids by evaporating the solvent, but the isolation process apparently changes them to some degree for some of the gelling or thickening properties are lost when the solids are redissolved. They are best handled as concentrates of up to about 50 percent by weight.

EXAMPLES 2-6

Several mixed dialkyl magnesium phosphates were prepared by reacting 0.4 g. of magnesium hydroxide with 5 g. of the dialkyl hydrogen phosphate at various temperatures and different reaction times, with and without added water, and otherwise as described in Example 1. Gel formation and the elasticity of the gel where formed was determined in each case. The results are listed in Table 1. Examples A, B, and C were run outside the process conditions for purpose of comparison.

Table 1

| Example No. | Alkyl Groups | Reaction Cond. Time | Temp. °C. | Water Added | Gel |
|---|---|---|---|---|---|
| 2 | t-butyl, dodecyl | 5 min. | 140 | 0 | Strong |
| 3 | t-butyl, dodecyl | 5 min. | 140 | 5 drops | Strong |
| 4 | t-butyl, dodecyl | 30 min. | 120 | 6 drops | Good |
| A | t-butyl, dodecyl | 2 hrs. | 100 | 0 | None |
| 5 | ethyl, dodecyl | 30 min. | 140 | 0 | Good |
| B* | ethyl, dodecyl | 2 hrs. | 140 | 0 | None |
| 6 | isopropyl, cetyl | 30 min. | 120 | 0 | Strong |
| C | isopropyl, cetyl | 3 hrs. | 50 | 0 | None |

*0.6 g. $Mg(OH)_2$ was reacted.

When magnesium hydroxide was reacted with dioctyl hydrogen phosphate and didodecyl hydrogen phosphate under the conditions of Examples 3-5, no gel was formed.

EXAMPLES 7-16

Various magnesium dialkyl phosphates prepared essentially as shown in Example 1 were dissolved in different solvents at a concentration of 0.25 percent by weight and the viscosities of the solutions were measured periodically while being stored at room temperature. Results are listed in Table 2.

Table 2

| Solvent | Mg Dialkyl Phosphate | Initial | 7 Days | 14 Days | 30 Days |
|---|---|---|---|---|---|
| Kerosene | None | 6[1] | 6 | 6 | 6 |
| Kerosene | isopropyl, cetyl | 41 | 76 | 85 | 77 |
| Kerosene | t-butyl, dodecyl | 36 | 69 | 90 | 87 |
| Kerosene | isopropyl, dodecyl[2] | 38 | 63 | 77 | 86 |
| Kerosene | isopropyl, dodecyl[3] | 12 | 27 | 34 | 36 |
| Kerosene | isopropyl, octadecyl | 9[1] | 12 | 14 | 27 |
| 1,1,1-Trichloroethane | None | 5[1] | 5 | 5 | 5 |
| 1,1,1-Trichloroethane | isopropyl, dodecyl | 15 | 18 | 22 | 21 |
| 1,1,1-Trichloroethane | isopropyl, octadecyl | 12 | 15 | 15 | 15 |
| Hexane | None | 3[1] | 3 | 3 | 3 |
| Hexane | isopropyl, cetyl | 10 | — | 30 | 34 |
| $CCl_4$ | None | 7[1] | 7 | 7 | 7 |
| $CCl_4$ | isopropyl, dodecyl | 15 | 13 | 14 | 21 |
| $CCl_4$ | isopropyl, cetyl | 64 | 85 | 91 | 91 |

[1] readings below 10 unreliable
[2] prepared by reacting 0.5 mole of $Mg(OH)_2$ with a mole of dialkyl phosphate
[3] prepared by reacting 0.33 mole of $Mg(OH)_2$ with a mole of dialkyl phosphate

EXAMPLES 17-23

Some of the solutions of the foregoing Examples 7-16 were checked for vapor pressure depression resulting from the presence of the magnesium dialkyl phosphate. These figures are listed in Table 3.

Table 3

| Solvent | Mg Dialkyl Phosphate | Vapor Pressure mm Hg at 23° C. |
|---|---|---|
| $CCl_4$ | None | 98 |
| $CCl_4$ | isopropyl, dodecyl | 73 |
| $CCl_4$ | isopropyl, cetyl | 71 |
| Hexane | None | 137 |
| Hexane | isopropyl, cetyl | 116 |
| 1,1,1-Trichloroethane | None | 102 |
| 1,1,1-Trichloroethane | isopropyl, dodecyl | 83 |
| 1,1,1-Trichloroethane | isopropyl, octadecyl | 93 |

In all cases, the magnesium dialkyl phosphate reduced the vapor pressure significantly.

We claim:
1. A process for making a magnesium salt of a dialkyl acid phosphate of the formula

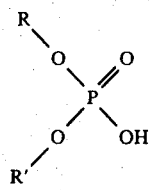

wherein R is an alkyl radical of about 1–6 carbon atoms, R' is an alkyl radical of about 10–20 carbon atoms, and R and R' together contain about 12–24 carbon atoms, which process comprises reacting magnesium in the form of its oxide, hydroxide, or carbonate with a molar excess of said dialkyl acid phosphate in an inert nonpolar organic solvent at about 100°–190° C. for 1–90 minutes in the presence of about 2–6 moles of water per mole of magnesium.

2. The process of claim 1 wherein the solvent is a normally liquid hydrocarbon or chlorinated hydrocarbon.

3. The process of claim 1 wherein the temperature is 120°–150° C. and the reaction time is 5–30 minutes.

4. The magnesium dialkyl phosphate product of the process of claim 1.

* * * * *